US00PP31463P2

(12) United States Plant Patent
van Langen

(10) Patent No.: US PP31,463 P2
(45) Date of Patent: Feb. 18, 2020

(54) ***ECHEVERIA* PLANT NAMED 'TSAECH1826'**

(50) Latin Name: ***Echeveria* hybrid**
Varietal Denomination: TSAECH1826

(71) Applicant: Tosjami B.V., Heerhugowaard (NL)

(72) Inventor: Gerard van Langen, Heerhugowaard (NL)

(73) Assignee: Tosjami B.V., Heerhugowaard (NL)

( * ) Notice: Subject to any disclaimer, the term of this patent is extended or adjusted under 35 U.S.C. 154(b) by 0 days.

(21) Appl. No.: 16/501,057

(22) Filed: Feb. 14, 2019

(51) Int. Cl.
*A01H 5/12* (2018.01)
*A01H 6/32* (2018.01)

(52) U.S. Cl.
USPC ..... Plt./373
CPC ..... *A01H 6/32* (2018.05); *A01H 5/12* (2013.01)

(58) Field of Classification Search
USPC ..... Plt./373
CPC ..... A01H 5/12
See application file for complete search history.

*Primary Examiner* — Kent L Bell
(74) *Attorney, Agent, or Firm* — Samuel R. McCoy, Jr.

(57) ABSTRACT

A new and distinct *Echeveria* plant named 'TSAECH1826' which is characterized by succulent foliage which is somewhat loosely held in a compact stemless rosette, lightly glaucous, greyed-green foliage which is distally margined and tipped greyed-purple, and the stability of these characteristics from generation to generation.

4 Drawing Sheets

Latin name of the genus and species: The Latin name of the genus and species of the novel variety disclosed herein is *Echeveria* hybrid.

Variety denomination: The inventive variety of *Echeveria* disclosed herein has been given the variety denomination 'TSAECH1826'.

BACKGROUND OF THE INVENTION

Parentage: 'TSAECH1826' is a seedling selection resulting from the controlled pollination of *Echeveria agavoides* 'Miranda' (Netherlands Plant Breeder's Rights application number ECH1; not patented in the United States), the seed parent, with an unnamed and unpatented *Echeveria pulidonis* plant, the pollen parent. The crossing was made by the inventor in the spring of 2014 at a commercial greenhouse in Heerhugowaard, the Netherlands. In the summer of 2015, one seedling resulting from the cross of 2014 was observed to exhibit unique growth and foliage characteristics and was isolated for further evaluation in order to confirm the distinctness and stability of the characteristics first observed. Upon confirmation of distinctness and stability, 'TSAECH1826' was selected for commercialization.

Asexual Reproduction: Asexual reproduction of the new cultivar 'TSAECH1826', by way of rooting leaf cuttings, was first initiated in the autumn of 2016 at the inventor's commercial greenhouse in Heerhugowaard, the Netherlands. Through four subsequent generations, the unique features of this cultivar have proven to be stable and true to type.

SUMMARY OF THE INVENTION

The cultivar 'TSAECH1826' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'TSAECH1826'. These characteristics in combination distinguish 'TSAECH1826' as a new and distinct *Echeveria* cultivar:

1. 'TSAECH1826' exhibits succulent foliage which is somewhat loosely held in a compact stemless rosette; and
2. 'TSAECH1826' exhibits small, narrowly obovate to oblanceolate foliage with a relaxed attitude; and
3. 'TSAECH1826' exhibits lightly glaucous, greyed-green foliage which is distally margined and tipped greyed-purple.

BOTANICAL DESCRIPTION OF THE PLANT

Figure 1:
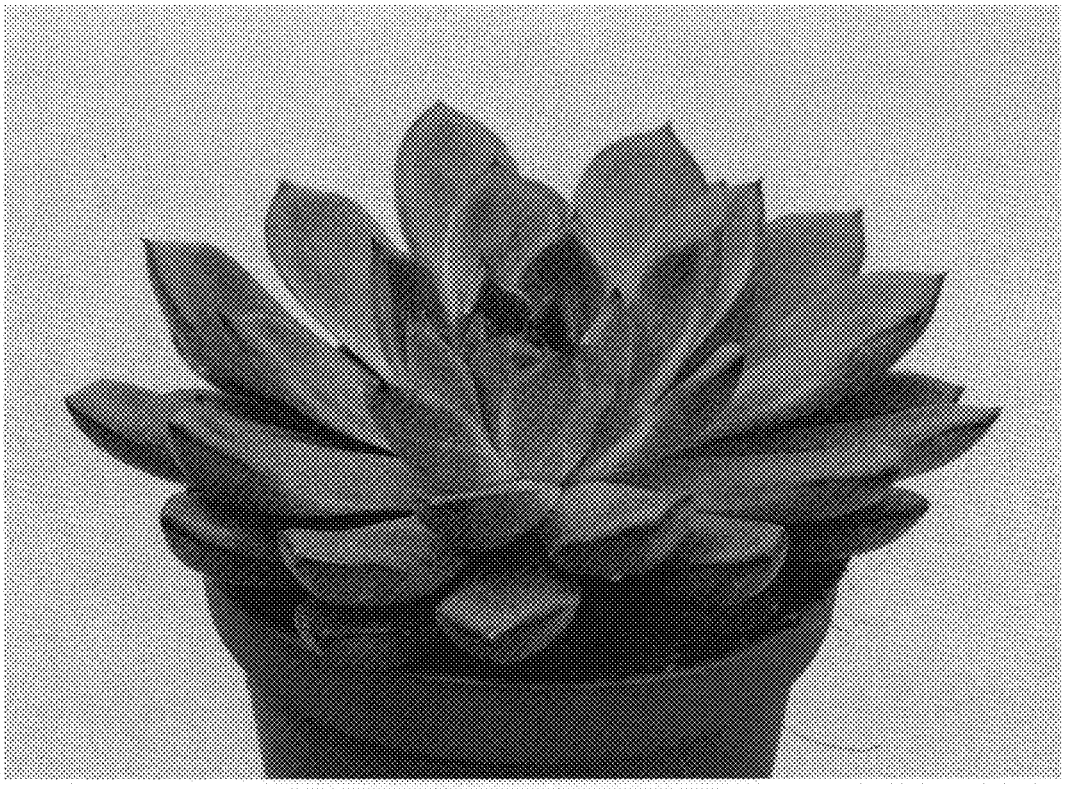
FIG. 1 illustrates, as nearly true as it is reasonably possible to make the same in color photographs of this type, an exemplary plant of 'TSAECH1826' grown in a commercial greenhouse in Heerhugowaard, the Netherlands. This plant is approximately 12 months old, shown planted in a 12 cm container.
Figure 2:
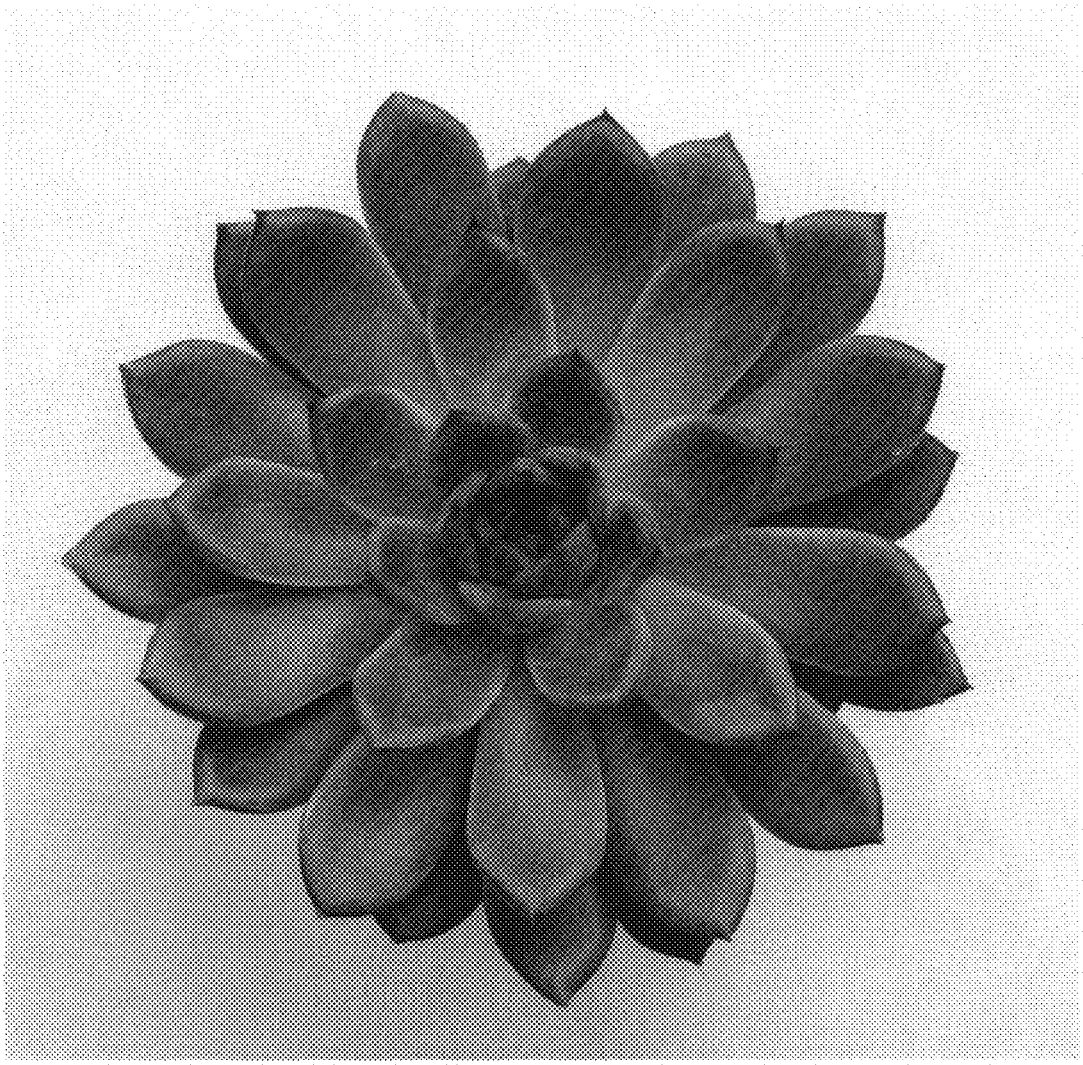
FIG. 2 illustrates, as nearly true as it is reasonably possible to make the same in color photographs of this type, the typical foliage arrangement of 'TSAECH1826.
Figure 3:
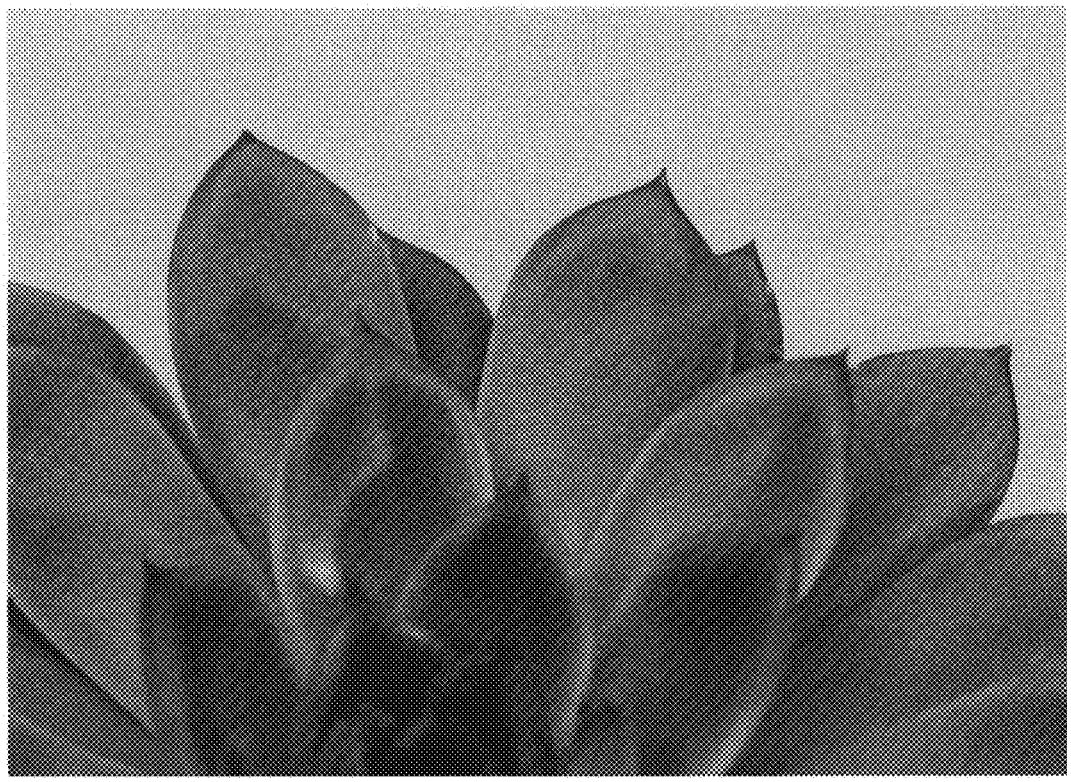
FIG. 3 illustrates, as nearly true as it is reasonably possible to make the same in color photographs of this type, the adaxial surface of the juvenile and mature foliage of 'TSAECH1826'.
Figure 4:
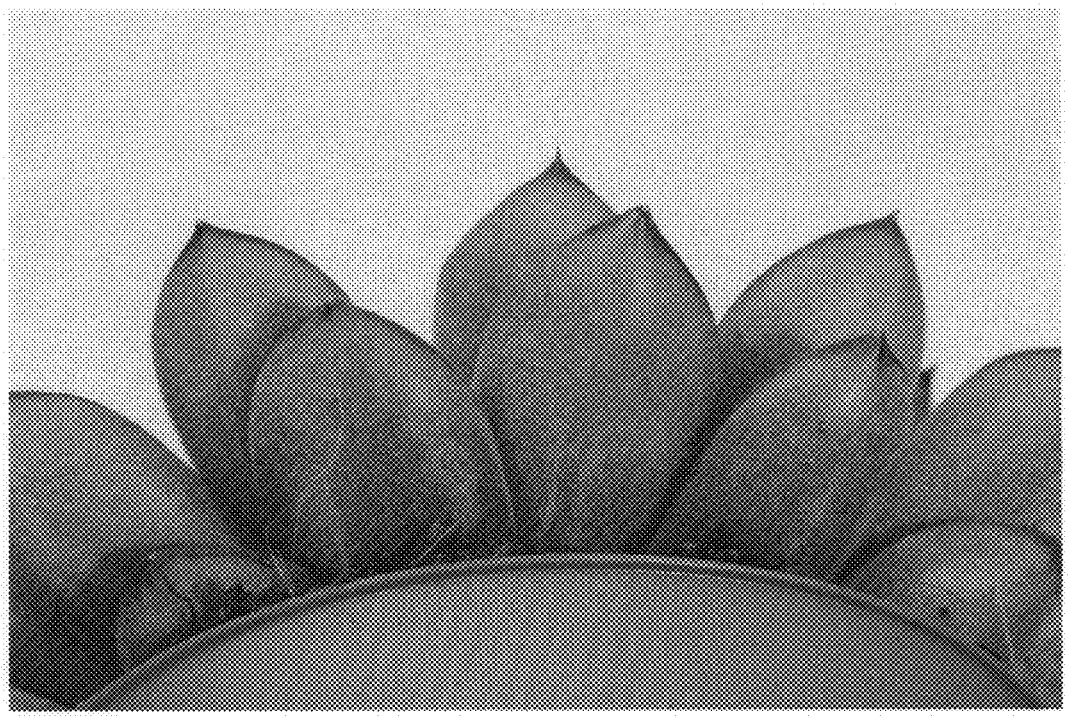
FIG. 4 illustrates, as nearly true as it is reasonably possible to make the same in color photographs of this type, the abaxial surface of the mature foliage of 'TSAECH1826'.

The following observations and measurements made in December of 2018 describe averages from a sample set of six specimens of 12 months old 'TSAECH1826' plants grown in 10.5 cm nursery containers at commercial greenhouse in Heerhugowaard, the Netherlands. Plants were produced using conventional greenhouse production protocols for *Echeveria* plants which consisted of minimal irrigation and fertilizer applications, and chemical pest and disease control measures against mealy bug and *Botrytis* as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'TSAECH1826' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'TSAECH1826' and comparisons with the parent plants and closest known comparator are provided below.

Plant description:

*Growth habit*.—Succulent perennial with foliage growing in a stemless basal rosette.

*Plant shape*.—Flattened.

*Height from soil level to top of foliar plane*.—4.2 cm.

*Plant spread*.—Average of 13.9 cm.

*Growth rate*.—Slow to moderately fast growing.

*Plant vigor*.—Moderately vigorous.

*Propagation*.—Type — Leaf cuttings. Time to initiate rooting — Approximately 21 days at 18 degrees Celsius. Crop time — Approximately 35 weeks to produce a marketable plant in a 10.5 cm container.

*Disease and pest resistance or susceptibility*.—Neither resistance nor susceptibility to typical *Echeveria* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Foliage:

*Arrangement*.—Rosette.

*Division*.—Simple.

*Attachment*.—Sessile.

*Quantity*.—Approximately 48 leaves per rosette.

*Shape*.—Narrow obovate to oblanceolate.

*Dimensions*.—5.8 cm long, 2.1 cm wide, and 0.9 cm thick, on average.

*Aspect*.—Slightly concave and very slightly curved upwards.

*Attitude*.—Juvenile foliage at the center of the rosette is held outward; foliage becomes progressively more relaxed towards the outer whorls of mature foliage, at an average angle of 20 degrees from horizontal.

*Apex*.—Apiculate.

*Base*.—Long cuneate.

*Margin*.—Entire; not undulated.

*Pubescence, texture and luster of the adaxial surface*.—Glabrous, smooth, and matte; lightly glaucous.

*Pubescence, texture and luster of the abaxial surface*.—Glabrous, smooth, and matte; lightly glaucous.

*Color*.—Juvenile foliage, adaxial surface — Nearest to in between green and greyed-green, RHS 137B and 191A, and fading to a lighter shade of yellow-green towards the base, nearest to in between RHS 145C and 145D; tipped greyed-purple, nearest to RHS 184A; the epicuticular wax covering the leaf surface is greyed-green, nearest to RHS 191B. Juvenile foliage, abaxial surface — Yellow-green, nearest to in between RHS 147B and 148B, and fading to a lighter shade of yellow-green towards the base, nearest to RHS 145D; tipped greyed-purple, nearest to a mixture of RHS 185A and 185B; the epicuticular wax covering the leaf surface is greyed-green, nearest to RHS 191B. Mature foliage, adaxial surface — Nearest to in between green and yellow-green, RHS NN137C and 147A, and fading to a lighter shade of yellow-green towards the base, nearest to RHS 146D; distally margined greyed-purple, nearest to a mixture of RHS 183A and 183B; the epicuticular wax covering the leaf surface is greyed-green, nearest to RHS 191B. Mature foliage, abaxial surface — Yellow-green, nearest to in between RHS 147B and 148B, and fading to a lighter shade of yellow-green towards the base, nearest to RHS 147D; distally margined greyed-purple, nearest to a mixture of RHS 183A and 183B; the epicuticular wax covering the leaf surface is greyed-green, nearest to RHS 191B.

*Venation*.—No venation is visible.

*Petiole*.—No petiole; leaves are sessile.

Inflorescence: No flowering has been observed to date.

Comparisons With the Parent Plant and Closest Known Comparator

Plants of the new cultivar 'TSAECH1826' differ from the seed parent, *Echeveria agavoides* 'Miranda' (Netherlands Plant Breeder's Rights application number ECH1; not patented in the United States), in the following characteristics described in Table 1 below.

TABLE 1

| Characteristic | 'TSAECH1826' | 'Miranda' |
|---|---|---|
| Plant size. | Smaller than 'Miranda'. | Larger than 'TSAECH1826'. |
| Foliage size. | Smaller than 'Miranda'. | Larger than 'TSAECH1826'. |
| General coloration of the foliage. | A darker shade of greyed-green. | A lighter shade of greyed-green. |
| General coloration of the foliage margins and apex. | Distally margined and tipped greyed-purple. | Broadly tipped red-purple. |

Plants of the new cultivar 'TSAECH1826' differ from the pollen parent, an unnamed *Echeveria pulidonis* plant (not patented), in the following characteristics described in Table 2 below.

TABLE 2

| Characteristic | 'TSAECH1826' | Pollen parent |
|---|---|---|
| Foliage attitude. | More upright. | More relaxed. |
| Plant shape. | Flattened. | Globular. |

TABLE 2-continued

| Characteristic | 'TSAECH1826' | Pollen parent |
|---|---|---|
| General coloration of the foliage. | Greyed-green. | In between blue-grey and blue-green. |

Comparisons With the Closest Known Comparator

Plants of the new cultivar 'TSAECH1826' differ from the closest known commercial comparator, *Echeveria agavoides* 'Red Tip' (not patented), in the following characteristics described in Table 3 below.

TABLE 3

| Characteristic | 'TSAECH1826' | 'Red Tip' |
|---|---|---|
| Growth habit. | More compact. | Less compact. |
| General coloration of the foliage. | Greyed-green. | Yellow-green. |

That which is claimed is:

1. A new and distinct variety of *Echeveria* plant named 'TSAECH1826', substantially as described and illustrated herein.

* * * * *